(12) United States Patent
Raptis et al.

(10) Patent No.: US 7,807,137 B1
(45) Date of Patent: *Oct. 5, 2010

(54) IRON-BASED CONTRAST AGENT

(75) Inventors: Raphael G. Raptis, San Juan, PR (US); Ricardo González-Méndez, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 1088 days.

This patent is subject to a terminal disclaimer.

(21) Appl. No.: 11/354,064

(22) Filed: Feb. 14, 2006

Related U.S. Application Data (63) Continuation-in-part of application No. 10/600,267, filed on Jun. 20, 2003, now Pat. No. 7,052,677, which is a continuation-in-part of application No. 09/470,504, filed on Dec. 22, 1999, now Pat. No. 6,596,259.

(60) Provisional application No. 60/113,537, filed on Dec. 22, 1998.

(51) Int. Cl.
*A61B 5/055* (2006.01)
*A61K 49/00* (2006.01)

(52) U.S. Cl. .................................. 424/9.1; 424/9.32
(58) Field of Classification Search .................. 424/9.32
See application file for complete search history.

(56) References Cited

U.S. PATENT DOCUMENTS

| | | | |
|---|---|---|---|
| 4,385,174 A | 5/1983 | Iqbal et al. | |
| 4,730,064 A | 3/1988 | Halbert et al. | |
| 5,141,855 A | 8/1992 | Schmittou | |
| 5,194,626 A | 3/1993 | Rolf et al. | |
| 5,364,953 A | 11/1994 | Beaty et al. | |
| 5,482,699 A | 1/1996 | Almen et al. | |
| 5,554,357 A | 9/1996 | Rajagopalan | |
| 5,614,168 A | 3/1997 | Berg et al. | |
| 5,624,662 A | 4/1997 | Unger et al. | |
| 5,850,086 A | 12/1998 | Que, Jr. et al. | |
| 5,892,033 A | 4/1999 | Komamura et al. | |
| 5,932,190 A | 8/1999 | Almen et al. | |
| 6,596,259 B1 | 7/2003 | Raptis | |
| 7,052,677 B1 * | 5/2006 | Raptis et al. | ............... 424/9.32 |

OTHER PUBLICATIONS

Mario V. Capparelli, Paul Hodge, and Brian Piggott. X-Ray cristallographic structure of $Ga_8(pz)_{12}O_4Cl_4$2thf: a novel gallium pyrazololate complex with a $Ga_4O_4$ core—*Chem. Commun.*, 1997. pp. 937-938.
Raphael G. Raptis, Irene P. Georgakaki, David C. R. Hockless; *Angew. Chem. Int. Ed.*, 38, No. 11, pp. 1632-1634 (1999).
Sergiu M. Gorun, Stephen J. Lippard; *Inorganic Chemistry*, vol. 30, No. 7, pp. 1625-1630 (1991).
F. Albert Cotton, L.M. Daniela, L. R. Falvello, J. H. Matonic, C. A. Murillo, X. Wang, H. Zhou; *Inorganica Chimica Acta* 266 , pp. 91-102 (1997).
Wolfgang Micklitz, Stephen J. Lippard; J., *Am. Chem. Soc.*, 111, pp. 6856-6858 (1989).
Katerina Dimitrou, Jui-Sui Sun, Kirsten Folting, George Christou; *Inorg. Chem.*, 34, pp. 4160-4166 (1995).
F. Albert Cotton, Stan A. Duraj, Wiewlaw J. Roth; *Inorg. Chem.*, 23, pp. 4042-4045 (1984).
Martin K. Ehlert, Steven J. Rettig, Alan Storr, Robert C. Thompson, James Trotter; *Acta Cryst.* C-50, pp. 1023-1026 (1994).
Steven C. Shoner, Philip P. Power; *Inorg. Chem.*, 31, pp. 1001-1010 (1992).
Kingsley L. Taft, Andrea Caneschi, Laura E. Pence, Christopher D. Delfs, Georgia C. Papaefthymiou, Stephen J. Lippard; *J. Am. Chem. Soc.*, 115, pp. 11753-11766 (1993).
Kingsley L. Taft, Georgia C. Papaefthymiou, Stephen J. Lippard; *Science*, vol. 259, pp. 1302-1305 (Feb. 1993).
Kingsley L. Taft, Georgia C. Papaefthymiou, Stephen J. Lippard; *Inorg. Chem.*, 33, pp. 1510-1520 (1994).
Hellmut Beinert, Richard H. Holm, Eckard Munck; *Science*, vol. 277, 1, pp. 653-659 (Aug. 1997).
Michael W. Willer, Jeffrey R. Long, Craig C. McLauchlan, R. H. Holm; *Inorganic Chemistry*, vol. 27, No. 2, pp. 328-333 (1998).
0. M. Yaghi, Z. Sun, D. A. Richardson, T. L. Groy; *J. Am. Chem. Soc.*, 116, pp. 807-808 (1994).
George M. Whitesides, John P. Mathias, Christopher T. Seto; *Science*, vol. 254, pp. 1312-1319 (Nov. 1991).

* cited by examiner

*Primary Examiner*—Michael G Hartley
*Assistant Examiner*—Melissa Perreira
(74) *Attorney, Agent, or Firm*—Hoglund & Pamias, PSC; Roberto J. Rios (57) ABSTRACT

A contrast agent having a metal core and an inert shell forming a single cluster is disclosed. The metal core is iron-based and has an octa-nuclear structure. It is surrounded by a cluster of pyrazolate groups. Ligands can be attached to the cluster to provide water solubility and to target specific tissues or provide specific contrast properties.

23 Claims, 10 Drawing Sheets

IRON-BASED CONTRAST AGENT

PRIORITY

This application claims priority to U.S. provisional application No. 60/113,537, filed Dec. 22, 1998, and to U.S. utility application Ser. No. 09/470,504, filed Dec. 22, 1999 and 10/600,267 filed Jun. 20, 2003. Each of these is incorporated herein by reference in their entirety.

GOVERNMENT INTERESTS

The claimed invention was made with Government support under grant number 5506GM08102-30S1 awarded by the National Institutes of Health (NIH). The Government has certain rights in this invention.

FIELD OF THE INVENTION

The invention relates generally to contrast agents that are used to enhance differentiation between adjacent tissues and organs in nuclear magnetic resonance imaging.

BACKGROUND OF THE INVENTION

Medical diagnostic imaging has evolved as an important non-invasive tool for medical diagnosis. Nuclear magnetic resonance imaging ("MRI") and computerized tomography ("CT") are two of the most widely used imaging methods. MRI generally relies on the relaxation properties of excited hydrogen nuclei in water. When the tissues or organs to be imaged are placed in a powerful, uniform magnetic field, the spins of the hydrogen protons within the tissues or organs align along the axis of the magnetic field.

The tissue is then briefly exposed to pulses of electromagnetic energy (RF pulse) in a plane perpendicular to the magnetic field, causing some of the magnetically aligned hydrogen nuclei to assume a temporary non-aligned high-energy state. As the high-energy nuclei relax and realign, they emit energy which is recorded to provide information about their environment. The realignment with the magnetic field is termed longitudinal relaxation and the time in milliseconds required for a certain percentage of the tissue nuclei to realign is termed "Time 1" or T1. This is the basis of T1-weighted imaging. T2-weighted imaging relies upon local dephasing of spins following the application of the transverse energy pulse; the transverse relaxation time is termed "Time 2" or T2. Both T1- and T2-weighted images are acquired for most medical examinations.

MRI takes advantage of the fact that water relaxation characteristics vary from tissue to tissue, and this tissue-dependent relaxation effect provides image contrast, which in turn allows the identification of various distinct tissue types. In order to create an image, spatial information must be recorded along with the received tissue relaxation information. A computer applies an inverse Fourier transform to this information so that it is converted into real space to obtain the desired image. This produces detailed anatomical information of the tissues or organs under inspection.

A modern MRI scanner will include a complex library of RF pulse sequences, each of which is optimized to provide image contrast based on the chemical sensitivity of MRI. The amount of time between successive pulse sequences is commonly referred to as the repetition time (TR). Another measurement used to characterize the RF pulse sequences is the echo time (TE). By varying these two parameters, the MRI scanner can produce T1-emphasized images or T2-emphasized images. A relatively short TR, on the order of a hundred to several hundred milliseconds, when combined with a relatively short TE, on the order of ten milliseconds, typically will produce T1-emphasized image. A relatively longer TR, on the order of a thousand milliseconds or longer, when combined with a relatively longer TE, on the order of ten to a hundred milliseconds, will produce a T2-emphasized image.

In order to increase the signal-to-noise ratio ("SNR"), a typical MRI scan is repeated at a constant rate for a predetermined number of times and the data is subsequently averaged. The signal amplitude recorded for any given scan is proportional to the number of spins that have decayed back to equilibrium in the time period between successive scans. Thus, regions with rapidly relaxing spins (i.e. those regions comprising spins having short T1 values) will recover all of their signal amplitude between successive scans. The measured intensities of the regions with long T2 and short T1 will reflect the spin density, which correlates with the region's water content. Regions with long T1 values, as compared to the time between scans, will progressively lose signal until a steady state condition is reached. At the steady state condition, the signal will be indistinguishable from background noise.

Although MRI can be performed without the administration of contrast agents, the ability to enhance the visualization of internal tissues and organs has resulted in their widespread use. Paramagnetic contrast agents effect a change in the relaxation characteristics of protons. In other words they can serve to modulate T1 and/or T2 values. This is particularly useful for imaging adjacent soft tissues, which may be histologically different but magnetically similar. An MRI scan obtained without the use of a contrast agent may not substantially differentiate between such adjacent soft tissues. If a contrast agent is localized in one of the two adjacent tissues, however, the imaging contrast can be substantially improved.

When designing or selecting contrast agents, two fundamental properties must be considered: a) biocompatibility, and b) proton relaxation enhancement. Biocompatibility is influenced by several factors including toxicity, stability (thermodynamic and kinetic), pharmacokinetics and biodistribution. Proton relaxation enhancement and relaxivity is chiefly governed by the metal employed in the agent, the rotational correlation times and the accessibility of the metal to surrounding water molecules, which permits the rapid exchange of metal-associated water molecules with the bulk solvent. The contrast agents most widely used are based upon ligand-stabilized gadolinium ions. Commercially available examples of these include Omniscan (gadodiamide), which is commercially available from Amersham Health, and ProHance (gadoteridol), which is commercially available from Bracco Diagnostics. Another widely used contrast agent is based upon sugar-coated iron-oxide (magnetite, $Fe_3O_4$) nanoparticles. This is commercially available from Mallinckrodt as GastroMARK (ferumoxsil). Another iron-based contrast agent is available from Berlex as Feridex (ferumoxides).

SUMMARY OF THE INVENTION

This invention relates to a metal-based cubane structure contained in an octanuclear complex which can be used as a contrast agent. More specifically, this complex can be defined as $Fe_8(\mu_4\text{-O})_4(\mu\text{-4-R-pz})_{12}L_4$, where:

Fe represents an iron atom having a +2, +3 or +4 oxidation state;

$\mu_4$-O represents a quadruply bridging oxygen atom;

$\mu$-4-R-pz represents a bridging pyrazolate ligand substituted at the 4 position by a group R, where R is any atom (including hydrogen) or group of atoms attached by a single bond to the pyrazole, for example organic groups, halogens, alkyls, aryls and other examples given below; and L is any terminal ligand, such as and for example only F, Cl, Br, NCO, NCS, alkyl, aryl, alkoxy or any anionic or neutral ligand or any combination of four terminal ligands.

One object of the present invention is to provide a contrast agent that is more physiologically acceptable to the human body. To this end, iron atoms are used to provide paramagnetic properties instead of gadolinium.

Another object of the present invention is to provide a contrast agent that can be designed to target specific tissues or organs. Specifically, in the above formula defining the composition of the complex, the R group (as well as the terminal ligand L) can be selected so that concentrations of the contrast agent are localized in a particular tissue or organ, which improves imaging of that tissue or organ.

According to one aspect of the invention, a water-soluble contrast agent is especially suitable for use in magnetic resonance imaging. The contrast agent is made of an octanuclear iron-pyrazolate cluster that reduces T1 of water by a factor of at least two with a concentration of 1 mM. The octanuclear iron-pyrazolate cluster is given by the formula:

$$Fe_8(\mu_4\text{-}O)_4(\mu\text{-}4\text{-}R\text{-}pz)_{12}L_4$$

where the portion of the compound identified as $\mu_4$-O is a quadruply bridging oxygen atom, where the portion of the compound identified as $\mu$-4-R-pz is a bridging pyrazole ring having a substituent group R bonded at the 4 position of the pyrazole ring, and the portion of the compound identified as L is a terminal ligand.

According to another aspect of the invention, the substitutent group R is a hydrophilic group. It can be selected from the following: $CH_2CH_2OH$, $CH_2CH_2CH_2OH$, $CO_2CH_3$, $CO_2CH_2CH_3$.

According to another aspect of the invention, the substituent group R is a hydrophobic group and the contrast agent includes a surfactant for water solubility. The R group can be selected from the following: Cl, Br, I, $CH_3$, $CH_2CH_2Cl$, $CH_2CH_2Br$, $CH_2CH_2CH_2Cl$ and $CH_2CH_2CH_2Br$. The surfactant can be selected from the following: a cyclodextrin and polyoxyethylene products of hydrogenated vegetable oils, polyethoxylated castor oils or polyethoxylated hydrogenated castor oil.

According to further aspects of the invention, the water-soluble contrast agent also reduces T2 by a factor of at least two with a concentration of 1 mM. It reduces T1 and T2 by a factor of at least ten with a concentration of 2 mM.

According to still further aspects of the invention, the substitutent group R is iodine so that the water-soluble contrast agent exhibits contrast enhancement in computer tomography.

DETAILED DESCRIPTION OF THE INVENTION

An octanuclear iron-pyrazolate cluster is used to provide paramagnetic properties in a contrast agent. The cluster has a core, which is the source of the paramagnetic properties, encapsulated in a protective shell. The structural integrity of the present cluster is a function of its composition. Specifically, the desired paramagnetic properties are a function of the metal core, while the connections required for the construction of variants take place at the outer inert shell. Further details of the octanuclear iron-pyrazolate cluster, which is used to provide the paramagnetic properties in a contrast agent, are now described. This is followed by a description of methods of preparing a number of variants and then specific results from the use of the clusters as contrast agents.

Octanuclear Iron-Pyrazolate Cluster

To achieve paramagnetic properties in a compound that is stable and has the versatility of accepting various groups, metal atoms must be complexed by appropriate ligands. More specifically, a complex comprising eight metal atoms protected inside a chemically inert shell. This complex can be used as a contrast agent in magnetic resonance imaging (MRI) applications.

One preferred composition is represented by the following formula (I):

$$Fe_8(\mu_4\text{-}O)_4(\mu\text{-}4\text{-}R\text{-}pz)_{12}L_4 \qquad (1)$$

where:

Fe is in any of the +2, +3 or +4 oxidation states;

$\mu_4$-O represents a quadruply bridging oxygen atom;

$\mu$-4-R-pz represents a bridging pyrazolate ligand substituted at the 4 position by a group R, where R is any atom or group of atoms attached by a single bond to the pyrazole, for example organic groups, halogens, alkyls, aryls and other examples given below; and L is any terminal ligand, such as and for example only F, Cl, Br, NCO, NCS, alkyl, aryl, alkoxy or any anionic or neutral ligand or any combination of four terminal ligands. As used hereinafter, a bridging pyrazolato group comprises any pyrazole either substituted or unsubstituted. The complex can be in a racemic, an enantiomerically-enriched or an enantiomerically-pure form.

Figure 1:
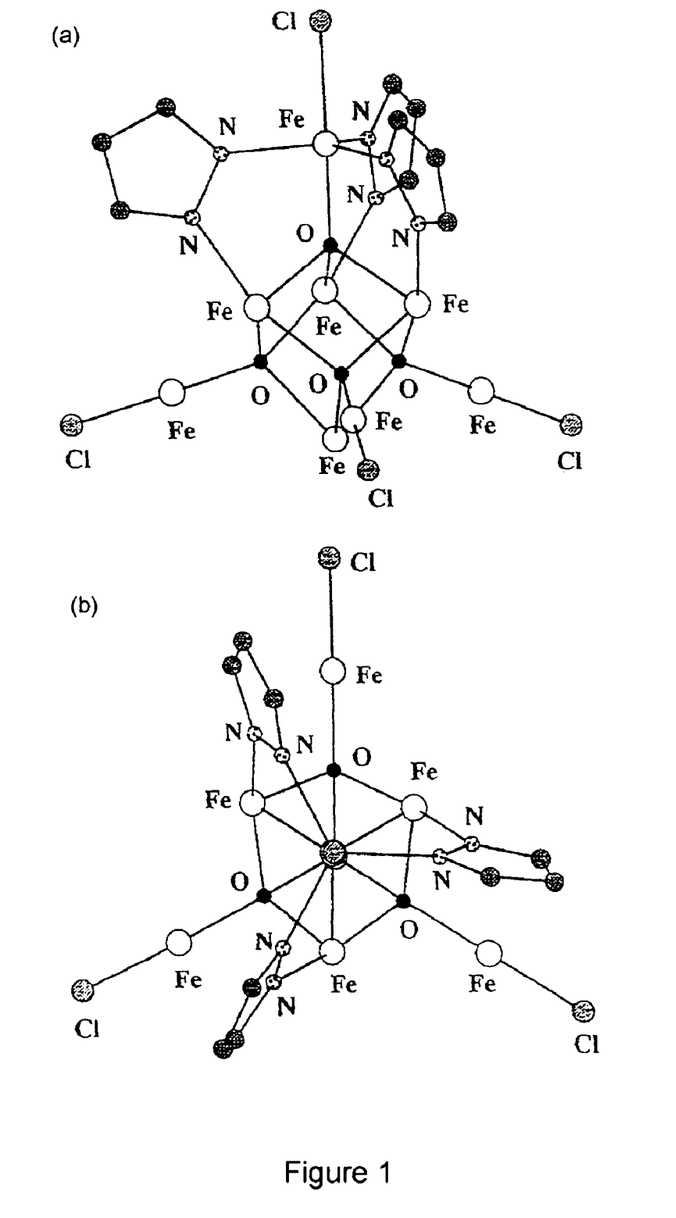
FIG. 1(a) illustrates the $Fe_8O_4Cl_4$ part of a complex of formula (1), and of three of the twelve pyrazolato groups therein.
FIG. 1(b) illustrates the same complex shown in FIG. 1(a), but is viewed parallel to a $C_3$-axis.
Figure 2:
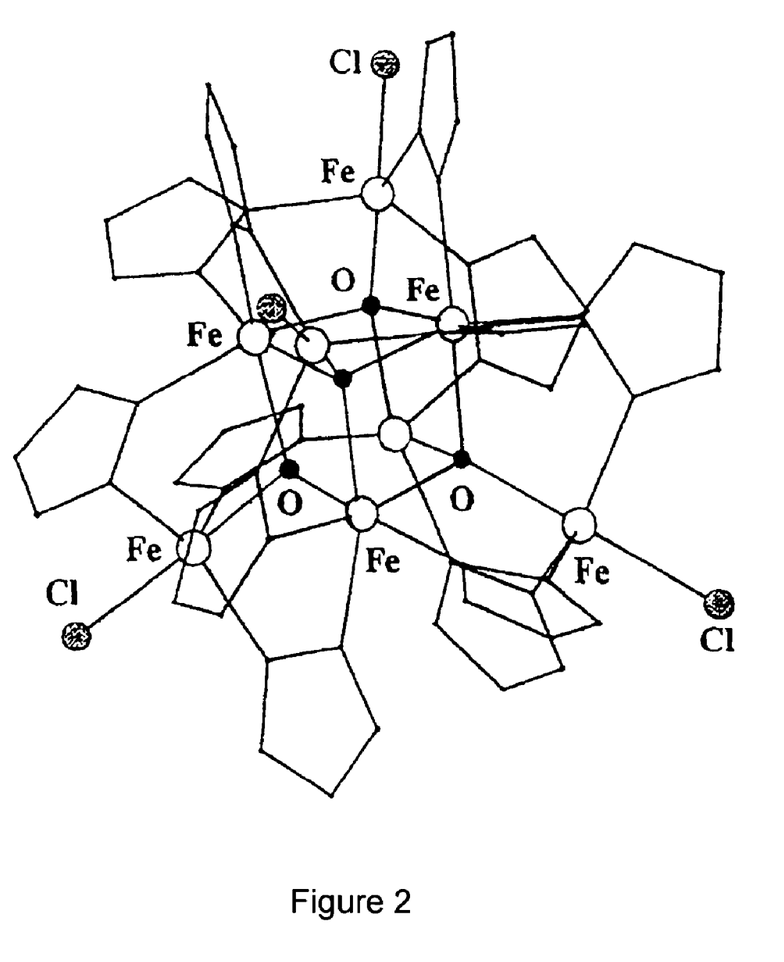
FIG. 2 illustrates the structure of a complex of formula (I) comprising spherical atoms of arbitrary radii. Hydrogen atoms are not shown.

One specific formulation is designated as follows:

where:

Fe represents Fe(III);

pz represents a pyrazolato anion, $C_3H_3N_2$; and

μ represents a bridging group, i.e., a bridging pz, or a bridging atom, such as an oxygen atom. This specific composition contains an octanuclear $Fe_8$ core, protected inside a pyrazolate coating. It is shown in FIGS. 1(*a*), 1(*b*) and 2.

Figure 3:
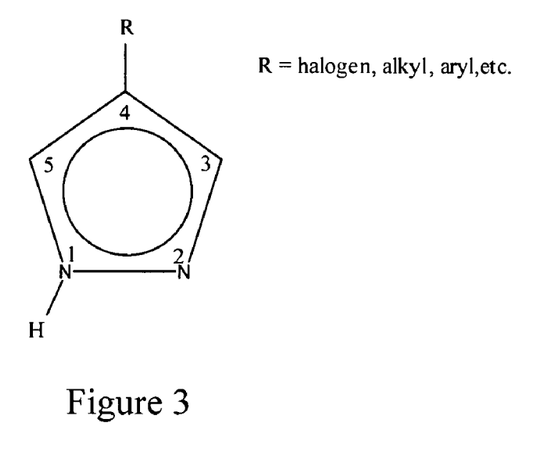
FIG. 3 illustrates a pyrazolato group.

Manipulation of the solubility of the inventive complex is possible through substitution at the outer shell. This can be done through substitution at either the positions of the terminal ligands, or the 4-position of the pyrazoles. A pyrazole ring substituted at the four position is shown in FIG. 3.

While one preferred form of the complex is hydrophobic, i.e., insoluble in water, but soluble in a large number of organic solvents, it can easily become water soluble by attaching hydrophilic groups to its surface through such substitutions. A second method to achieve water-soluble preparations of the $Fe_8$-complex is through the use of surfactants. Water-soluble derivatives of the inventive complex are particularly useful as MRI contrast agents. Methods of making specific formulations are now described.

Preparation of Fe(III) Complexes

Example 1

The starting materials that can be used to prepare the $Fe_8$ $(μ_4-O)_4(μ-pz)_{12}Cl_4$ complex defined by formula (I) include the following commercially available materials: anhydrous ferric chloride ($FeCl_3$), pyrazole ($C_3H_4N_2$, pzH) and triethylamine. Also, sodium pyrazolate (Na-pz), or potassium pyrazolate (K-pz) can be readily prepared from pyrazole and sodium hydride or potassium hydride. Either pyrazolate works equally well. Other common reagents can be used as pyrazolate-transfer agents in the preparation of formula (1).

A typical preparation of the example is as follows: To a suspension of $FeCl_3$ (3.120 g; 19.23 mmol) in $CH_2Cl_2$ (200 mL) was added solid Napz (2.598 g; 28.85 mmol) under an Ar atmosphere with stirring. To the resulting dark brown solution, triethylamine (1.340 mL; 9.617 mmol) was added dropwise with stirring under argon. After 20 h, the dark brownish-red reaction mixture was exposed to air, sealed again and kept stirring for an additional 24 h period. After filtration, an unidentified dark brown solid (a minor product) was disposed and the dark red filtrate was allowed to slowly evaporate to dryness at 23° C. under air. The resulting solid was washed with acetone (50 mL) and recrystallized twice from $CH_2Cl_2$ (140 mL and 70 mL). A dark red crystalline solid was collected by filtration, washed with methanol, and dried. Yield: 1.07 g (30%). (b) To a suspension of $FeCl_3$ (0.910 g; 5.61 mmol) in $CH_2Cl_2$ (43 mL) prepared under an argon atmosphere was added solid pyrazole (1.146 g; 16.83 mmol) under air with stirring. An orange crystalline solid of $Fe(pzH)_3Cl_3$ was formed within 60 seconds. Triethylamine (1.955 mL; 14.03 mmol) was added dropwise with stirring. All orange solid was dissolved and the reaction mixture turned dark red. After stirring for 13 hours a dark brownish-red mixture was filtered. A solid portion was disposed and the resulting dark red solution was let to evaporate slowly to dryness at 23° C. The resulting solid was washed with methanol (10 mL) and recrystallized from $CH_2Cl_2$ (22 mL) under air. The obtained dark red crystalline solid (0.469 g) was recrystallized from another portion of $CH_2Cl_2$ (15 mL) under the nitrogen atmosphere. Big dark red crystals were collected by filtration, washed with methanol, and dried. Testing demonstrated that this was the desired product.

Example 2

A typical preparation of the example is as follows: To a suspension of $FeCl_3$ (0.197 g; 1.21 mmol) in $CH_2Cl_2$ (30 mL) prepared under an argon atmosphere was added solid 4-Cl-pyrazole (0.374 g; 3.64 mmol) under air with stirring. To the pale red solution was added dropwise with stirring triethylamine (0.423 mL; 3.04 mmol). After stirring for 5 min a dark red mixture was filtered and liquid part was placed into a Schlenk tube and stirred under nitrogen for 2 days, when the stirring was interrupted. In 2 months, regular octahedral dark orange crystals of the product together with colorless needles of triethylammonium chloride were collected. Then the solid mixture was recrystallized from acetone (15 mL), and subsequently from $CH_2Cl_2$ (4 mL). Product was collected by filtration, washed with methanol, and dried. Testing demonstrated that this was the desired product.

Example 3

A typical preparation of the example is as follows: To a suspension of $FeCl_3$ (0.967 g; 5.96 mmol) in $CH_2Cl_2$ (200 mL) prepared under an argon atmosphere was added dropwise 4-Me-pyrazole (1.48 mL; 17.9 mmol) under air with stirring. To the pale red solution was added dropwise with stirring triethylamine (2.08 mL; 14.9 mmol). After stirring for 20 hours a dark orange mixture was filtered. Testing demonstrated that this was the desired result.

Example 4

A typical preparation of the example is as follows: To a suspension of $FeBr_3$ (0.371 g; 1.26 mmol) in $CH_2Cl_2$ (15 mL) prepared under an argon atmosphere was added solid pyrazole (0.256 g; 3.77 mmol) under air with stirring. To the red solution was added dropwise with stirring triethylamine (0.437 mL; 3.14 mmol). After stirring for 10 Min the mixture was filtered and filtrate was placed into a Schlenk tube and stirred under nitrogen for 6 days. The volume of the reaction mixture was reduced to 5 mL under vacuum, stirred overnight and filtered under nitrogen. The filtrate was evaporated to dryness, washed with methanol (22 mL) and recrystallized from diethyl ether (40 mL) and subsequently from $CH_2Cl_2$ (6 mL). Product was collected by filtration, washed with methanol, and dried Other Examples Preparation of Other Fe(III) Complexes can be Obtained by Substitution of the terminal ligand Cl or Br, and/or by substitution on the 4 position of the pyrazole groups. Specifically, the terminal ligands can be substituted by F, Br, SCN, OCN, OPh (where Ph is a phenyl group either substituted or unsubstituted, i.e., $C_6H_5$, $C_6H_4R$, $C_6H_4X$), py (where py is a pyridine group, $C_6H_5N$, or substituted pyridine group, i.e., $C_6H_4NR$, $C_6H_4NX$), or a metal or metal complex such as Ag, Cu, Pd or Pt. Alternatively, the terminal ligand can be substituted by a bridging ligand including pyrazine, or bipyridine. With the substitution of bridging ligands multiple Fe(III) complexes are joined.

Each of these examples includes a metal, cubane core and in inert shell, as shown in FIG. 3. The inert shell includes four terminal ligands, L, which can be selected to target specific tissues or organs. In addition, the 4-position of the pyrazole groups can be substituted as shown in FIG. 3. Specifically, the 4-position is substituted by a halogen (including, e.g., F, Cl, Br, I) or a pseudo-halogen (including, e.g., CN). Alternatively, the 4-position is substituted by an organic group, which include all variations of $C_nH_{2n+1}$, $C_nH_{2n-1}$, $C_nH_{2n-3}$, $C_nH_{2n}X$, $C_nH_{2n-1}X_2$, $C_nH_{2n-2}X_3$, $C_nH_{2n-2}X$, $C_nH_{2n-3}X_2$, $C_nH_{2n-4}X_3$, $C_nH_{2n-4}X$, $C_nH_{2n-5}X_2$, $C_nH_{2n-6}X_3$. The parameter n is typically less than 40. X can be F, Cl, Br, I, CN, OH, $NH_2$, $SO_3H$, $PO_4H_2$ or CHO. Two or three different groups X can be combined in the same compound.

MRI Contrast Agents

Following the above methods, a library of iron-cluster compounds having different R-groups at the pyrazole 4-position can be obtained. These include compounds having hydrophobic R-groups such as, R=Cl, Br, Cl, Br, I, $CH_3$, $CH_2CH_2Cl$, $CH_2CH_2Br$, $CH_2CH_2CH_2Cl$ or $CH_2CH_2CH_2Br$. To use these as a contrast agent in medical applications, they can be brought into aqueous solutions by mixing with commercially available surfactants, such as cyclodextrins, or polyoxyethylene products of hydrogenated vegetable oils, polyethoxylated castor oils or polyethoxylated hydrogenated castor oil. Alternatively, directly water-soluble clusters can be prepared by the introduction of hydrophilic groups such as, R=$CH_2CH_2OH$, $CH_2CH_2CH_2OH$, $CO_2CH_3$ or $CO_2CH_2CH_3$.

For example, the R=$CH_2CH_2CH_2OH$, L=Cl compound can prepared. Specifically, a round bottomed flask is charged under an $N_2$-atmosphere with 0.400 g (2.47 mmol) $FeCl_3$ in ethanol and an ethanolic solution of 0.464 g (4.32 mmol) 4-$HO(CH_2)_3$-pzH and 0.093 g (4.93 mmol) $Et_3N$. The solution is stirred for 24 hours in the air and the product is crushed-out by $Et_2O$ addition and filtered. The filtered solid is washed three times with small portions of $CH_2Cl_2$, followed by washing, three times, with acetone. The hygroscopic dark red solid product is dried under vacuum and stored under $N_2$. This yields a water-soluble iron-cluster compound.

A further advantage of the R=$(CH_2)_nOH$ derivatives is that they provide a route to the synthesis of targeted agents by the attachment of directing groups (via the chemically functional OH) to the contrast agent module.

Figure 4:
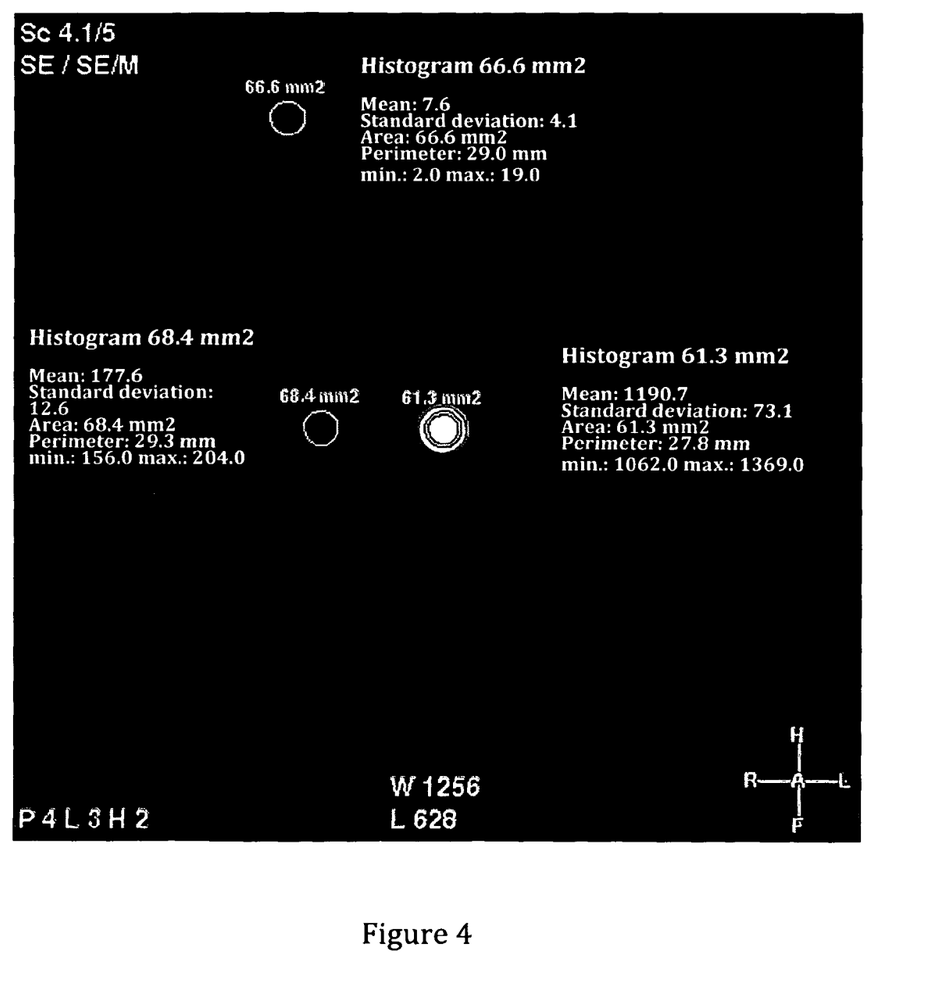
FIG. 4 is an image taken with an MRI machine showing phantoms consisting of a vial containing $H_2O$ (center left) and an aqueous solution of a water-soluble preparation of the $Fe_8$-complex (center right).

MRI experiments demonstrate that a tenfold reduction in T1 of water can be achieved using these compositions. For example, a 5 mM-$H_2O$ solution shows a contrast-to-noise ratio of approximately 250, exceeding the necessary enhancement for clinical imaging. This is shown in FIG. 4. Specifically, this figure shows the contrast enhancement of the water-soluble iron-cluster at a 5 mM concentration in distilled water when compared to distilled water alone (the solvent). The bright circle on the right near the center is the sample containing the water-soluble iron-cluster, the grayish circle on the left near the center shows the distilled water control. Regions-of-interest (ROI) were identified on each to obtain the statistical information for the intensity of the pixels within the region. A ROI in the empty space (upper left ROI with no signal) was also drawn to measure the noise characteristics of the image. For the ROI in the water-soluble iron-cluster, the measured properties were:

|  | Water-Soluble Iron-Cluster | Distilled Water | Empty Space |
| --- | --- | --- | --- |
| Mean | 1190.7 | 177.6 | 7.6 |
| Standard Deviation | 73.1 | 12.6 | 4.1 |
| Area (mm$^2$) | 61.3 | 68.4 | 66.6 |
| Perimeter (mm) | 27.6 | 29.3 | 29.0 |
| Minimum | 1062.0 | 156.0 | 2.0 |
| Maximum | 1369.0 | 204.0 | 19.0 |

These values are used to calculate the contrast-to-noise ratio (CNR) defined as:

$$CNR = \frac{mean\_si\_cluster - mean\_si\_water}{sdnoise}$$

where mean_si_cluster is the mean of the signal intensity of the ROI for the enhanced image (1190.7), mean_si_water is the mean signal intensity of the ROI for the distilled water control (177.6), and sdnoise is the standard deviation of the ROI in the empty space (4.1) which represents a measure of the noise in the image. These values give a CNR of 247.1 for an MRI image take at a TR=200 msec and TE=10 msec.

Figure 5:
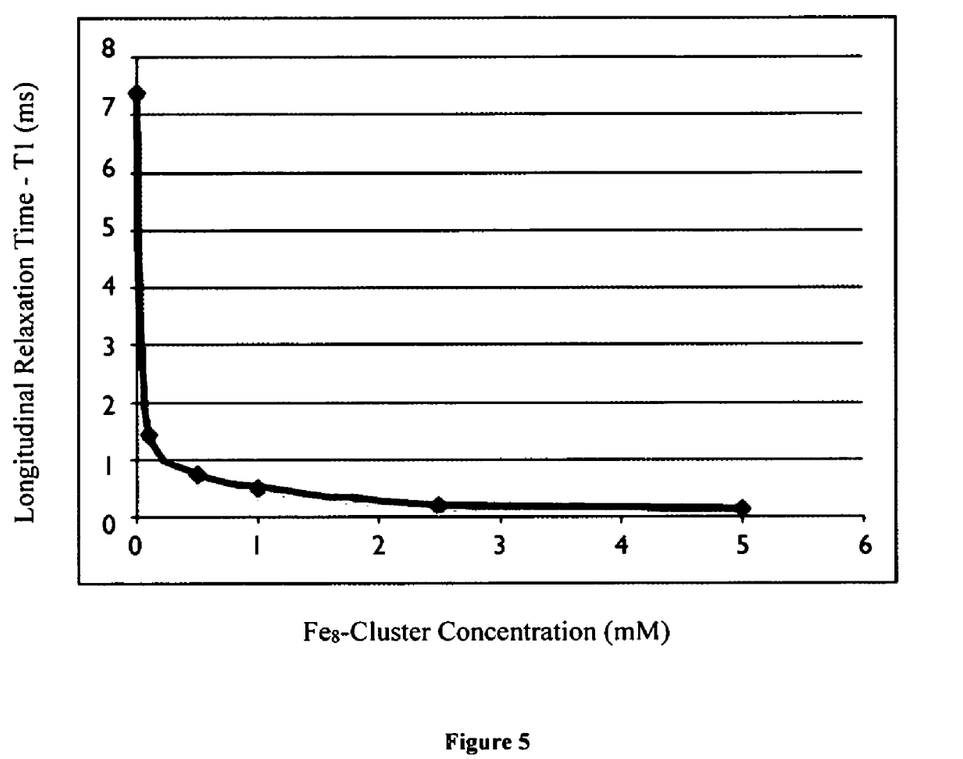
FIG. 5 is a graph of the longitudinal relaxation time, T1, in milliseconds (ms) (shown along the vertical axis), versus the concentration of the $Fe_8$-Cluster in milli-Molar (mM) units (shown along the horizontal axis).

In addition to providing good contrast-to-noise ration, the water-soluble iron-cluster also provides significant T1 and T2 effect. Turning to FIG. 5, T1 is plotted as a function of concentration. At zero concentration, distilled water exhibits a T1 over 7 seconds. As the concentration of the water-soluble iron-cluster is increased above 1 mM, T1 falls below 1 second. As the concentration is increased, T1 is reduced by over a factor of 10.

Figure 6:
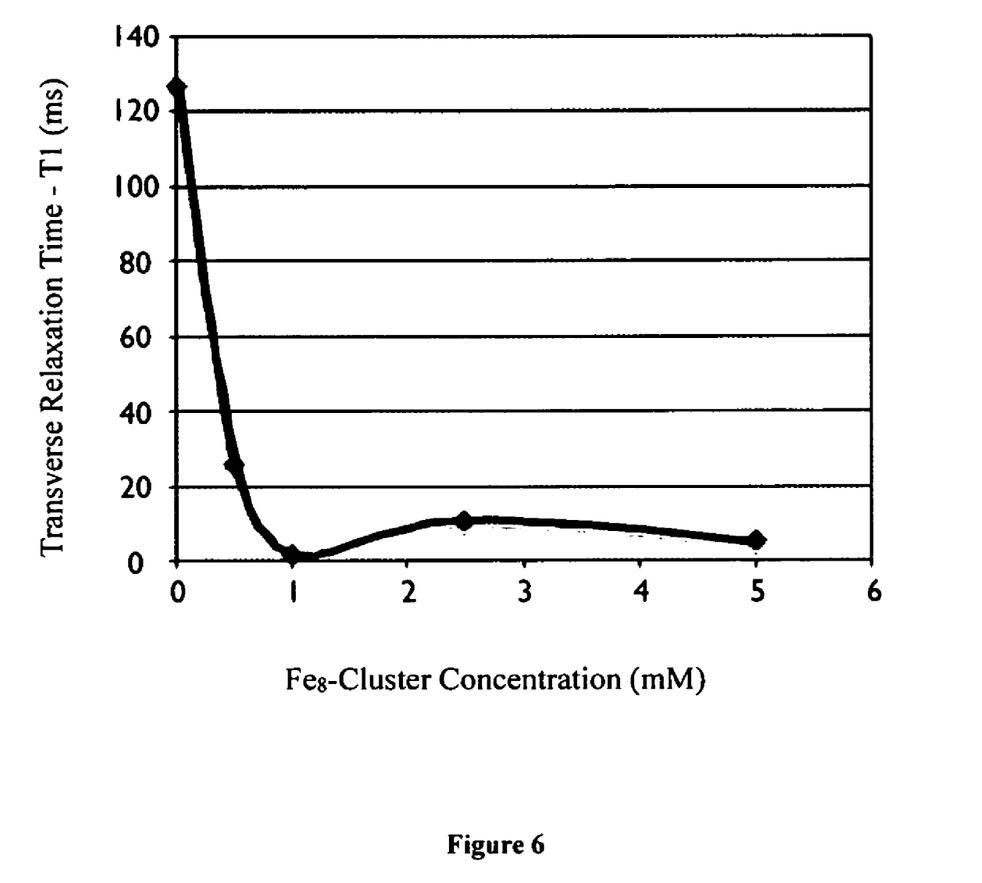
FIG. 6 is a graph of the transverse relaxation time, T2, in ms (shown along the vertical axis), versus the concentration of the $Fe_8$-Cluster in mM (shown along the horizontal axis).

Turning to FIG. 6, T2 is plotted as a function of concentration. At zero concentration, distilled water exhibits a T2 over 120 ms. As the concentration of the water-soluble iron-cluster is increased to 1 mM, T2 falls well below 5 ms, and remains approximately at or below 10 ms as the concentration is further increased. Thus, T2 can be reduced by over a factor of 20.

Turning to FIGS. 7(a)-7(d), an MRI image of vials containing various solutions are shown. In each of these figures, the top-most circle is a vial of solution containing an iodine derivative of the iron-cluster compound $Fe_8(\mu_4-O)_x(\mu-4-I-pz)_4(\mu-4-HO(CH_2)_3-pz)_yCl_4$, x+y=12. In the middle row, the left-most circle is a vial of a solution containing a gadolinium-based contrast agent; the middle circle is a vial containing a solution of the water-soluble iron-cluster at 5 mM; and the right-most circle is a vial containing distilled water. In the bottom row, the left-most circle is a vial of a solution containing a solution of the water-soluble iron-cluster at 0.5 mM; the middle circle is a vial of a solution containing the water-soluble iron-cluster at 1.0 mM; and the right-most circle is a vial containing a solution of the water-soluble iron-cluster at 5.0 mM.

For FIGS. 7(a)-(d), TR and TE were varied. The following table lists the settings:

|  | TR (ms) | TE (ms) |
|---|---|---|
| 7(a) | 100 | 15 |
| 7(b) | 3000 | 20 |
| 7(c) | 3000 | 60 |
| 7(d) | 3000 | 100 |

Figure 7A:
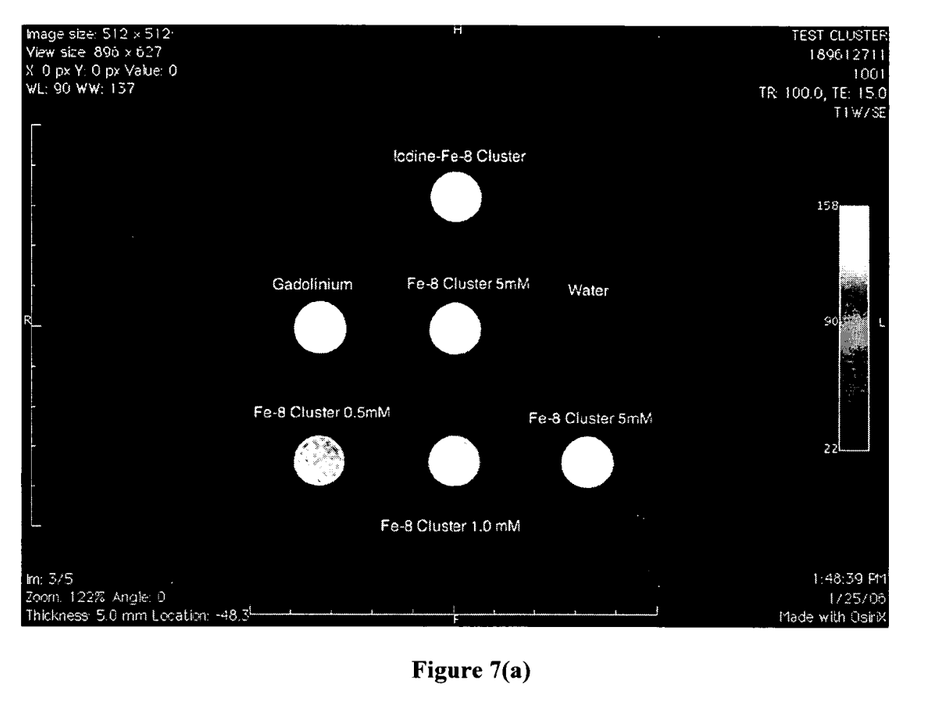
FIG. 7(a) is an image taken with an MRI machine showing phantom vials containing water, a gadolinium solution and various concentrations of the $Fe_8$-Cluster, where TR=100 ms and TE=15 ms.

In FIG. 7(a), each of the solutions exhibit a T1 effect and provide noticeable contrast with the vial containing only water.

Figure 7B:
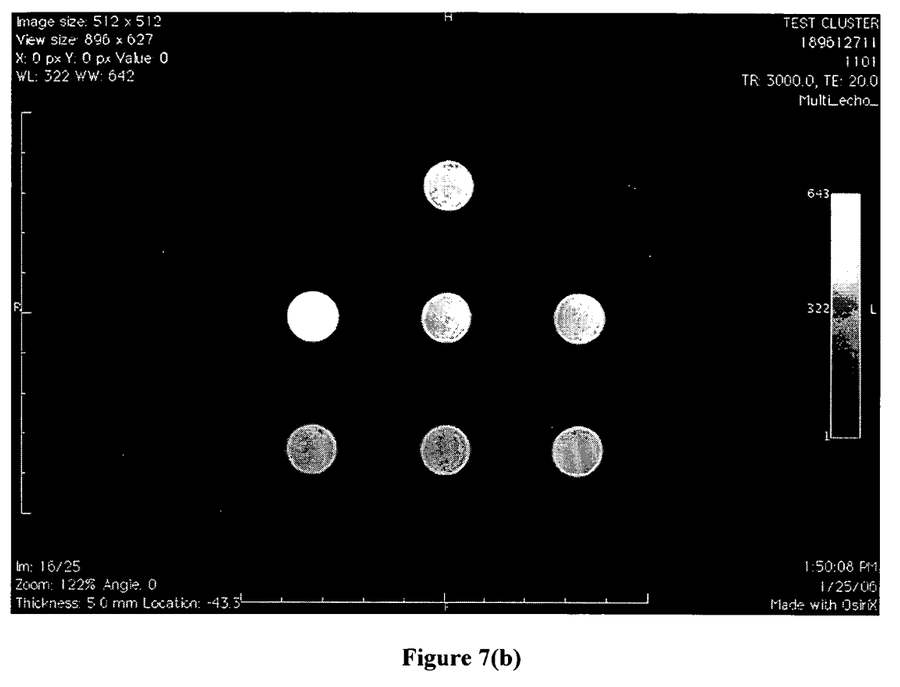
FIG. 7(b) is an image taken with an MRI machine showing the phantom vials of FIG. 7(a), where TR=3000 ms and TE=20 ms.

In FIG. 7(b) the gadolinium-based contrast agent does not appear to provide a T2 effect and has brightness similar to that of the vial containing only water. The vials containing a low-concentration of the water-based iron-cluster, however, exhibit a T2 effect.

Figure 7C:
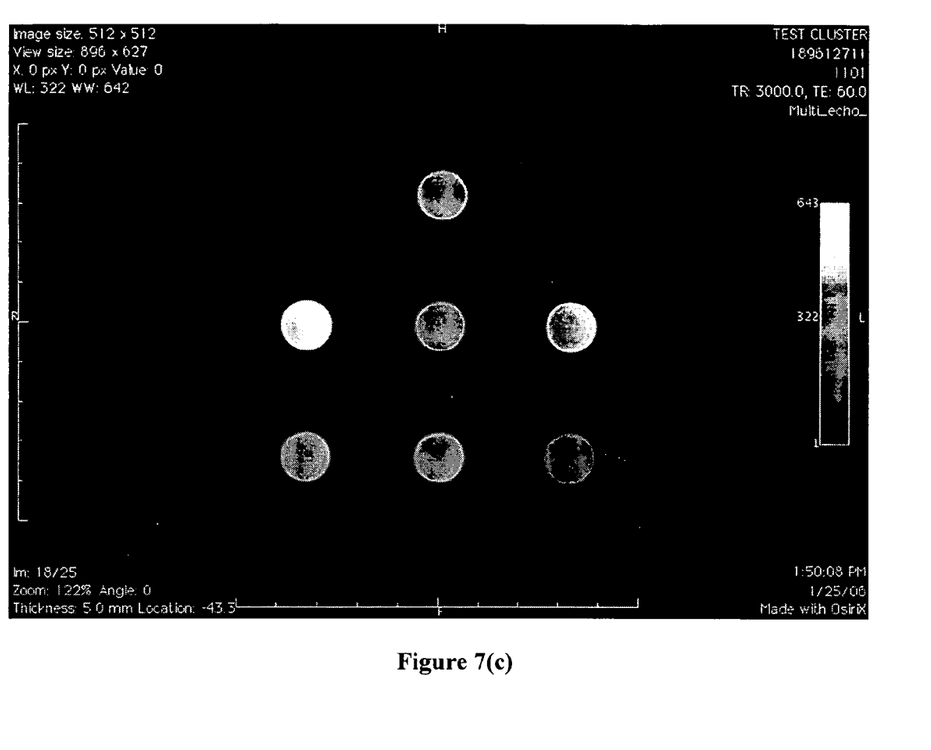
FIG. 7(c) is an image taken with an MRI machine showing the phantom vials of FIG. 7(a), where TR=3000 ms and TE=60 ms.
Figure 7D:
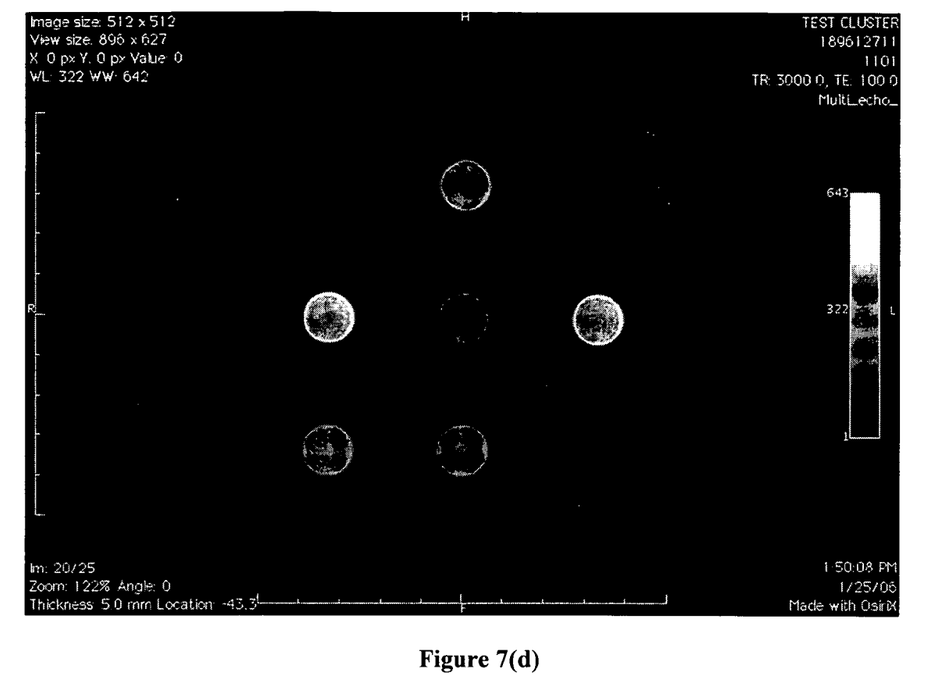
FIG. 7(d) is an image taken with an MRI machine showing the phantom vials of FIG. 7(a), where TR=3000 ms and TE=100 ms.

In FIGS. 7(c) and (d), as TE is increased, all of the solutions containing the iron-cluster exhibit noticeable contrast with the vial containing only water. The contrast is most pronounced for the longest TE of 100 shown in FIG. 7(d).

CT Contrast Agents

In addition to providing MRI contrast enhancement, iodine-containing derivatives of the Fe8-based contrast agent also provides contrast enhancement in computer tomography (CT). This has the advantage of only using one contrast agent for both imaging techniques, as opposed to employing two contrast agents. Suitable formulations for this purpose include:

$$Fe_8(\mu_4\text{-O})_4(\mu\text{-4-I-}pz)_x(\mu\text{-4-HO}-(CH_2)_2\text{-}pz)_yCl_4, \quad (1)$$

where x+y=12;

$$Fe_8(\mu_4\text{-O})_4(\mu\text{-4-I-}pz)_x(\mu\text{-4-HO}-(CH_2)_3\text{-}pz)_yCl_4, \quad (2)$$

where x+y=12;

$$Fe_8(\mu_4\text{-O})_4(\mu\text{-4-HO}-CH_2CHICH_2\text{-}pz)_{12}Cl_4; \quad (3)$$

$$Fe_8(\mu_4\text{-O})_4(\mu\text{-4-HO}-CH_2CH_2CHI\text{-}pz)_{12}Cl_4; \quad 1$$

$$Fe_8(\mu_4\text{-O})_4(\mu\text{-4-HO}-CH_2CHI\text{-pz})_{12}Cl_4; \text{ and} \quad (5)$$

$$Fe_8(\mu_4\text{-O})_4(\mu\text{-4-HO}(CH_2)_n\text{-}pz)_x(\mu\text{-4-HO}(CH_2)_m CHI\text{-}pz)_yCl_4, \quad (6)$$

Where x+y=12, n=2 or 3 and m=1 or 2.

We claim:

1. A water-soluble contrast agent especially suitable for use in magnetic resonance imaging comprising an octanuclear iron-pyrazolate cluster wherein the water-soluble contrast agent reduces a longitudinal relaxation time of water (T1) by a factor of at least two with a concentration of 1 mM.

2. The water-soluble contrast agent of claim 1, wherein the octanuclear iron-pyrazolate cluster comprises:

$$Fe_8(\mu_4\text{-O})_4(\mu\text{-4-R-}pz)_{12}L_4$$

where the portion of the compound identified as $\mu_4$-O is a quadruply bridging oxygen atom, where the portion of the compound identified as $\mu$-4-R-pz is a bridging pyrazole ring having a substituent group R bonded at the 4 position of the pyrazole ring, and the portion of the compound identified as L is a terminal ligand.

3. The water-soluble contrast agent of claim 2, wherein the substitutent group R comprises a hydrophilic group.

4. The water-soluble contrast agent of claim 3, wherein the substituent group R is selected from the group consisting of $CH_2CH_2OH$, $CH_2CH_2CH_2OH$, $CO_2CH_3$, $CO_2CH_2CH_3$.

5. The water-soluble contrast agent of claim 2, wherein the substituent group R comprises a hydrophobic group and wherein the contrast agent further comprises a surfactant.

6. The water-soluble contrast agent of claim 5, wherein the substituent group R is selected from the group consisting of Cl, Br, I, $CH_3$, $CH_2CH_2Cl$, $CH_2CH_2Br$, $CH_2CH_2CH_2Cl$ and $CH_2CH_2CH_2Br$.

7. The water-soluble contrast agent of claim 5, wherein the surfactant is selected from the group consisting of a cyclodextrin and polyoxyethylene products of hydrogenated vegetable oils, polyethoxylated castor oils or polyethoxylated hydrogenated castor oil.

8. The water-soluble contrast agent of claim 1, wherein the water-soluble contrast agent reduces the longitudinal relaxation time of water (T1) by a factor of at least ten with a concentration of 2 mM.

9. The water-soluble contrast agent of claim 1, wherein the water-soluble contrast agent reduces the transverse relaxation time of water (T2) by a factor of at least two.

10. The water-soluble contrast agent of claim 1, wherein the water-soluble contrast agent reduces the transverse relaxation time of water (T2) by a factor of at least ten with a concentration of 2 mM.

11. The water-soluble contrast agent of claim 2, wherein the substitutent group R comprises iodine and wherein the water-soluble contrast agent exhibits contrast enhancement in computer tomography.

12. A water-soluble contrast agent especially suitable for use in magnetic resonance imaging comprising an octanuclear iron-pyrazolate cluster wherein the water-soluble contrast agent reduces a transverse relaxation time of water (T2) by a factor of at least two with a concentration of 1 mM.

13. The water-soluble contrast agent of claim 12, wherein the octanuclear iron-pyrazolate cluster comprises:

$$Fe_8(\mu_4\text{-O})_4(\mu\text{-4-R-}pz)_{12}L_4$$

where the portion of the compound identified as $\mu_4$-O is a quadruply bridging oxygen atom, where the portion of the compound identified as $\mu$-4-R-pz is a bridging pyrazole ring having a substituent group R bonded at the 4 position of the pyrazole ring, and the portion of the compound identified as L is a terminal ligand.

14. The water-soluble contrast agent of claim 13, wherein the substitutent group R comprises a hydrophilic group.

15. The water-soluble contrast agent of claim 14, wherein the substituent group R is selected from the group consisting of $CH_2CH_2OH$, $CH_2CH_2CH_2OH$, $CO_2CH_3$, $CO_2CH_2CH_3$.

16. The water-soluble contrast agent of claim 13, wherein the substituent group R comprises a hydrophobic group and wherein the contrast agent further comprises a surfactant.

17. The water-soluble contrast agent of claim 16, wherein the substituent group R is selected from the group consisting of Cl, Br, I, $CH_3$, $CH_2CH_2Cl$, $CH_2CH_2Br$, $CH_2CH_2CH_2Cl$ and $CH_2CH_2CH_2Br$.

18. The water-soluble contrast agent of claim 16, wherein the surfactant is selected from the group consisting of a cyclodextrin and polyoxyethylene products of hydrogenated vegetable oils, polyethoxylated castor oils or polyethoxylated hydrogenated castor oil.

19. The water-soluble contrast agent of claim 12, wherein the water-soluble contrast agent reduces the transverse relaxation time of water (T2) by a factor of at least ten with a concentration of 2 mM.

20. The water-soluble contrast agent of claim 12, wherein the water-soluble contrast agent reduces the longitudinal relaxation time of water (T1) by a factor of at least ten with a concentration of 2 mM.

21. The water-soluble contrast agent of claim 13, wherein the substituent group R comprises iodine and wherein the water-soluble contrast agent exhibits contrast enhancement in computer tomography.

22. A water-soluble contrast agent especially suitable for use in magnetic resonance imaging comprising an octanuclear iron-pyrazolate cluster wherein the water-soluble contrast agent reduces a longitudinal relaxation time of water (T1) and a transverse relaxation time of water (T2) sufficient to produce detectable contrast in magnetic resonance imaging.

23. A contrast agent comprising a compound given by the formula:

$$Fe_8(\mu_4\text{-}O)_4(\mu\text{-}4\text{-}R\text{-}pz)_{12}L_4$$

where the portion of the compound identified as $\mu_4$-O is a quadruply bridging oxygen atom, where the portion of the compound identified as $\mu$-4-R-pz is a bridging pyrazole ring having a substituent group R bonded at the 4 position of the pyrazole ring, and the portion of the compound identified as L is a terminal ligand, wherein the contrast agent reduces a longitudinal relaxation time of water (T1) and a transverse relaxation time of water (T2) sufficient to produce detectable contrast in magnetic resonance imaging.

* * * * *